US012778857B2

(12) United States Patent
Hara et al.

(10) Patent No.: US 12,778,857 B2
(45) Date of Patent: Nov. 3, 2026

(54) ZIRCONIA DENTAL MILL BLANK, MANUFACTURING METHOD THEREFOR, METHOD FOR MANUFACTURING DENTAL ZIRCONIA CERAMIC PROSTHESIS, AND METHOD FOR MANUFACTURING ARTICLE COMPOSED OF ZIRCONIA COMPOSITE CERAMIC

(71) Applicant: TOKUYAMA DENTAL CORPORATION, Tokyo (JP)

(72) Inventors: Hiroshi Hara, Tokyo (JP); Akari Hashimoto, Tokyo (JP); Kei Nakashima, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 648 days.

(21) Appl. No.: 18/252,802

(22) PCT Filed: Oct. 22, 2021

(86) PCT No.: PCT/JP2021/039055
§ 371 (c)(1),
(2) Date: May 12, 2023

(87) PCT Pub. No.: WO2022/102372
PCT Pub. Date: May 19, 2022

(65) Prior Publication Data

US 2024/0000670 A1 Jan. 4, 2024

(30) Foreign Application Priority Data

Nov. 12, 2020 (JP) ................................ 2020-188760

(51) Int. Cl.
*A61K 6/818* (2020.01)
*A61C 13/00* (2006.01)
*A61C 13/083* (2006.01)
*A61K 6/822* (2020.01)

(52) U.S. Cl.
CPC .......... *A61K 6/818* (2020.01); *A61C 13/0006* (2013.01); *A61C 13/083* (2013.01); *A61K 6/822* (2020.01)

(58) Field of Classification Search
CPC .......... A61K 6/818; C04B 2111/00836; C04B 41/87; C04B 2235/3246
See application file for complete search history.

(56) References Cited

U.S. PATENT DOCUMENTS

2005/0164045 A1 7/2005 Rothbrust et al.
2005/0187638 A1 8/2005 Glien et al.
2008/0118894 A1* 5/2008 Rothbrust ........... C04B 41/4537 428/688
2008/0213725 A1* 9/2008 Adilstam ............. A61C 8/0012 427/2.27
2015/0175485 A1 6/2015 Gottwik et al.
2016/0310245 A1 10/2016 Fujisaki et al.
2017/0216000 A1* 8/2017 Jahns ...................... C04B 41/53
2020/0055779 A1 2/2020 Theelke et al.

FOREIGN PATENT DOCUMENTS

| | | | |
|---|---|---|---|
| JP | 2006500183 | A | 1/2006 |
| JP | 2006280564 | A | 10/2006 |
| JP | 2007507250 | A | 3/2007 |
| JP | 2007534368 | A | 11/2007 |
| JP | 2011178610 | A | 9/2011 |
| JP | 2015533754 | A | 11/2015 |
| JP | 2016117618 | A | 6/2016 |
| JP | 2017530939 | A | 10/2017 |
| JP | 6333254 | B2 | 5/2018 |
| JP | 2019508349 | A | 3/2019 |
| JP | 2019108289 | A | 7/2019 |
| JP | 2020079256 | A | 5/2020 |
| JP | 6720318 | B2 | 7/2020 |
| WO | 2005027771 | A1 | 3/2005 |
| WO | 2015098765 | A1 | 7/2015 |
| WO | 2016019114 | A1 | 2/2016 |
| WO | 2017114777 | A1 | 7/2017 |

OTHER PUBLICATIONS

Seiji Ban, "Complete Guidebook for CAD/CAM Materials: Clinical Useful Material Selection and Adhesive Operation," Ishiyaku Publishers, Inc., Dec. 20, 2017, pp. 18-20 (3 pages) with Partial English Translation.
Extended European Search Report issued in corresponding European Patent Application No. 21891619.5, dated Sep. 13, 2024 (5 pages).

* cited by examiner

*Primary Examiner* — Cameron K Miller
(74) *Attorney, Agent, or Firm* — Osha Bergman Watanabe & Burton LLP

(57) ABSTRACT

Provided are a zirconia dental mill blank and a manufacturing method therefor, said mill bank having a to-be-cut part composed of a composite material, which includes fine particles of an inorganic oxide (excluding zirconium oxide, an inorganic oxide functioning as a stabilizer, and aluminum oxide) and a matrix composed of a temporarily sintered body of a crystalline zirconium oxide powder containing a stabilizer and an aluminum oxide additive, wherein the temporarily sintered body is a microporous temporarily sintered body having a relative density of 45-65% and having pores opened outward, and the fine particles of the inorganic oxide are held in the pores of the microporous temporarily sintered body. Moreover, provided are a method for manufacturing a dental zirconia ceramic prosthesis, and a method for manufacturing an article composed of a zirconia composite ceramic.

5 Claims, No Drawings

ZIRCONIA DENTAL MILL BLANK, MANUFACTURING METHOD THEREFOR, METHOD FOR MANUFACTURING DENTAL ZIRCONIA CERAMIC PROSTHESIS, AND METHOD FOR MANUFACTURING ARTICLE COMPOSED OF ZIRCONIA COMPOSITE CERAMIC

TECHNICAL FIELD

The present invention relates to a zirconia dental mill blank and a manufacturing method therefor, a method for manufacturing a dental zirconia ceramic prosthesis, and a method for manufacturing an article composed of a zirconia composite ceramic.

BACKGROUND ART

Computer aided design (CAD) technology and computer aided manufacturing (CAM) technology are being introduced into the dental field due to the development of information communication technology in recent years. For example, with respect to the manufacturing of a tooth crown prosthesis, CAD/CAM systems for milling blanks for dental processing composed of nonmetal materials based on intraoral photographed images using CAM/CAD apparatuses to form dental prostheses have been increasingly frequently used. Here, the term "blanks for dental processing" means bodies to be milled that can be attached to milling machines in CAD/CAM systems (also referred to as mill blanks), which usually have milling target parts and holding parts for enabling milling target parts to be attached to milling machines. As the milling target parts, (solid) blocks molded into shapes such as cuboids and columns; (solid) disks formed into platy shapes or discoid shapes; and the like are commonly known.

Since a highly aesthetic dental prosthesis excellent in strength and toughness can be manufactured, as the nonmetal material, a zirconia-based ceramic material is often used. A completely sintered zirconia-based ceramic material is difficult to mill due to the strength thereof. When a dental prosthesis composed of the zirconia-based ceramic (hereinafter also referred to as a "zirconia prosthesis") is manufactured using a CAD/CAM system, as the milling target part of a zirconia dental mill blank (hereinafter also referred to merely as a "zirconia mill blank"), a zirconia-based ceramic preliminarily sintered body that has been preliminarily sintered at relatively low sintering temperature has therefore been commonly used. The preliminarily sintered body is milled into the shape corresponding to the shape of a prosthesis to be finally obtained by CAM based on CAD in view of shrinkage and the like that occur during final sintering at high temperature and then finally sintered to manufacture a zirconia prosthesis densified and highly strengthened.

Since pure zirconia (zirconium oxide) causes phase transition accompanied with the volume change depending on the temperature, stress due to volume change in the cooling process after the sintering may crack the zirconia-based ceramic to reduce the strength. Stabilized zirconia or partially stabilized zirconia enabled to exist as tetragonal crystals or a mixed crystal system of tetragonal crystals and cubic crystals, which is stable at high temperature, without transitioning to monoclinic crystals, which are stable at low temperature, even in cooling by adding a stabilizer such as yttrium oxide, calcium oxide, or magnesium oxide to prevent such phase transition has been developed. As a zirconia raw material powder to be used for a zirconia mill blank, such stabilized zirconia or partially stabilized zirconia is also used, and stabilized zirconia or partially stabilized zirconia to which aluminum oxide (additive) is further added for increasing the strength has been commonly used. For example, Patent Document 1 describes a "zirconia powder characterized in that the zirconia powder includes more than 4.0 mol % and 6.5 mol % or less yttria and less than 0.1 wt % alumina, and the BET specific surface area is 8 to 15 $m^2/g$" as a raw material powder that can give a zirconia sintered body having both translucency and strength suitable especially as an artificial tooth for a front tooth by pressureless sintering.

Incidentally, as shown in Non-Patent Document 1, it is known that, in the sintered body of (partially) stabilized zirconia in which yttria (yttrium oxide) is blended as a stabilizer, the adjustment of the added amount of yttria changes the existence ratio of tetragonal zirconia to cubic zirconia to change the strength or transparency according thereto. That is, as the content of yttria increases, the content of the cubic crystals, which contribute to improvement in transparency, increases, and the content of the tetragonal crystals, which contribute to increase in strength, decreases in response thereto. High strength and high transparency are therefore in the so-called trade-off relationship. Therefore, if a prosthesis for front teeth or the like, requiring high transparency, is manufactured, it is common to use "partially stabilized zirconia having an yttria content of 5 mol % or more", which has slightly inferior strength, by giving priority to the transparency, and if a prosthesis for molar portions, a long-span bridge with 4 units or more, or the like, requiring high strength, is manufactured, it is common to use "stabilized zirconia or partially stabilized zirconia having an yttria content of 3 mol % or less", which has inferior transparency. Thus, one zirconia mill blank cannot cope with all the dental prostheses from prostheses for front teeth to long-span bridges, a suitable zirconia-based ceramic preliminarily sintered body needs to be selected from zirconia-based ceramic preliminarily sintered bodies of different raw materials depending on the type of a prosthesis to be manufacture, and used.

Although some techniques for complexing a zirconia-based ceramic preliminarily sintered body that can be used as the milling target part of the zirconia mill blank for improving the physical properties of the finally obtained zirconia-based ceramic finally sintered body (completely sintered body) are also known, a zirconia-based ceramic material that can cope with all of prostheses for front teeth, prostheses for the molar portions, and long-span bridges, in other words, that becomes the milling target part of the mill blank that enables manufacturing all these prostheses that satisfy requirements in uses from one mill blank is unknown.

For example, Patent Document 2 discloses a technique for molding and then preliminarily sintering stabilized zirconia or partially stabilized zirconia in which strontium aluminate, spinel, or the like is blended at particularly preferably 4 to 6% by volume to improve the microscopic shear deformability (or resistance in polishing with a tool provided with diamonds) or the aging resistance to hot water of a completely sintered body. Patent Document 2 shows that a completely sintered body obtained by processing and then sintering the thus obtained preliminarily sintered body has a structure in which secondary phases including the above-mentioned strontium aluminate, spinel, or the like and having preferably particle sizes of 0.2 to 0.5 μm are dispersed in a zirconium oxide matrix layer having an average particle size of 0.1 to 2.0 μm, the hardness decreases (as compared with the case of completely sintered body having no secondary phases), the optimization of the amount of the secondary phases depending on the type of the secondary phases improves the fracture toughness and improves the residual strength after damage (Vickers hardness indenter), but does not examine the transparency.

Patent Document 3 discloses a technique involving manufacturing, as a zirconia blank, a preliminarily sintered body obtained by soaking an aqueous solution of $ZrOCl_2$ and further infiltrating an aqueous $NH_4OH$ solution into a preliminarily sintered body of stabilized zirconia to form $Zr(OH)_4$ for increasing the strength of a completely sintered body and drying the preliminarily sintered body. Patent Document 3 shows that, in an article obtained by sintering this, the flexural strength is improved as compared with a sintered body of stabilized zirconia sintered without such treatment, but does not examine the transparency, either.

Furthermore, Patent Document 4 discloses a technique involving infiltrating a penetrant including a sol obtained by mixing a catalyst composed of tetraethyl orthosilicate (TEOS) and aluminum nitrate nonahydrate into water, and the like into the surface portion of a stabilized or partially stabilized zirconia preliminarily sintered body, sintering the stabilized or partially stabilized zirconia preliminarily sintered body, and then etching the surface portion as a technique for improving the adhesiveness of a dental prosthesis composed of a zirconia-based ceramic. Patent Document 4 discloses that, in this technique, the (semi)transparency of the inside of the sintered body (into which the penetrant is not infiltrated) is equivalent to those of conventional items into which stabilized or partially stabilized zirconia is hot-isostatic pressed, and etching the surface enables providing more satisfactory adhesive fixability with an aesthetic effect that is the same as those of the conventional items. It is disclosed that, in the surface portion before the etching, the fracture toughness is improved, but the flexural strength or the transparency of only the surface portion is not examined.

Patent Document 1: PCT International Publication No. WO2015/098765

Patent Document 2: Japanese Patent No. 6333254

Patent Document 3: Japanese Patent No. 6720318

Patent Document 4: Japanese Unexamined Patent Application (Translation of PCT Application), Publication No. 2007-534368

Non-Patent Document 1: Seiji Ban, "CAD/CAM Material Perfect Guide Book, Material Selection and Adhesion Operation Useful for Clinical Practice", Ishiyaku Publishers, Inc., Dec. 20, 2017, pp. 18-20

DISCLOSURE OF THE INVENTION

Problems to be Solved by the Invention

As mentioned above, different zirconia dental mill blanks cannot but be used in the case where a prosthesis for a front tooth, wherein aesthetics (transparency) is valued, is manufactured and in the case where a prosthesis for a molar or a long-span bridge, required to have high strength, is manufactured under the present conditions.

Then, an object of the present invention is to provide a zirconia dental mill blank that can cope with the manufacturing of dental prostheses in various forms from one mill blank, a manufacturing method therefor, and a method for manufacturing an article such as a dental prosthesis composed of a zirconia composite ceramic, having satisfactory transparency and strength.

Means for Solving the Problems

Specific means for achieving the above-mentioned object includes the following embodiments.

<1> A zirconia dental mill blank, including a milling target part composed of a composite material, the composite material including:

a matrix including a preliminarily sintered body of crystalline zirconium oxide powder containing a stabilizer and an aluminum oxide additive; and fine particles of an inorganic oxide, provided that zirconium oxide, an inorganic oxide functioning as a stabilizer, and aluminum oxide are excluded, in which, in the composite material, the preliminarily sintered body is a microporous preliminarily sintered body having a relative density of 45 to 65% and having pores opened outward, and the fine particles of the inorganic oxide are held in the pores of the microporous preliminarily sintered body.

<2> The zirconia dental mill blank according to <1>, in which an average pore diameter of the microporous preliminarily sintered body measured by mercury penetration is in a range of 50 to 200 nm, and the fine particles of the inorganic oxide have an average primary particle diameter smaller than the average pore diameter.

<3> The zirconia dental mill blank according to <1> or <2>, in which, in the composite material, a content ratio of the fine particles of the inorganic oxide held in the pores of the microporous preliminarily sintered body is 0.09 to 10% by mass based on a total mass of the microporous preliminarily sintered body and the fine particles of the inorganic oxide.

<4> A method for manufacturing the zirconia dental mill blank according to any one of <1> to <3>, including:

a matrix manufacturing step of molding the crystalline zirconium oxide powder into a predetermined shape, and then preliminarily sintering the molded powder at 600 to 1200° C. to obtain the matrix;

a sorption step of immersing the matrix obtained in the matrix manufacturing step in a sol in which the fine particles of the inorganic oxide are dispersed in a dispersion medium and a concentration of the fine particles is 0.03 to 0.9% by mass based on a mass of the sol, to thereby sorb the fine particles of the inorganic oxide in the pores of the microporous preliminarily sintered body constituting the matrix; and a drying step of removing the dispersion medium from the matrix subjected to the sorption step.

<5> A method for manufacturing a dental zirconia ceramic prosthesis composed of a zirconia composite ceramic, wherein the zirconia composite ceramic has, as a basic structure, a structure in which aluminum oxide crystal grains as an additive are dispersed in a polycrystal structure formed by bonding of the same or different types of zirconia crystals in which a stabilizer is solid dissolved, and further includes an inorganic oxide, provided that zirconium oxide, an inorganic oxide functioning as a stabilizer, and aluminum oxide are excluded, a content ratio of the inorganic oxide contained in the zirconia composite ceramic is 0.09 to 10% by mass based on a mass of the zirconia composite ceramic, and in the basic structure, the inorganic oxide exists in at least one selected from a grain boundary between zirconia crystal grains adjoining each other and a grain boundary between a zirconia crystal grain and an aluminum oxide crystal grain adjoining, the manufacturing method including:

a milling step of milling a milling target part of the zirconia dental mill blank according to <1> to <3> using a CAD/CAM system to obtain a semifinished product having a shape corresponding to a shape of a target dental prosthesis and composed of the composite material; and a final sintering step of sintering the semifinished product at a temperature of more than 1200° C. and 1800° C. or less to change the composite material into the zirconia composite ceramic.

<6> The manufacturing method according to <5>, wherein biaxial flexure strength of the zirconia composite ceramic measured according to JIS T6526:2018 is 800 to 2000 MPa, and a contrast ratio is 0.5 to 0.8, the contrast ratio being an index of transparency, and being defined by the following expression:

$$\text{contrast ratio}=Yb/Yw$$

wherein Y means Y values obtained from a sample having a thickness of 1.0 mm±0.01 mm by spectral reflectance measurement using a spectrophotometer, and Yb and Yw represent the Y values measured with a background color black and a background color white, respectively.

<7> A method for manufacturing an article composed of a zirconia composite ceramic, wherein the zirconia composite ceramic has, as a basic structure, a structure in which aluminum oxide crystal grains as an additive are dispersed in a polycrystal structure formed by bonding of the same or different types of zirconia crystals in which a stabilizer is solid dissolved, and further includes an inorganic oxide, provided that zirconium oxide, an inorganic oxide functioning as a stabilizer, and aluminum oxide are excluded, a content ratio of the inorganic oxide contained in the zirconia composite ceramic is 0.09 to 10% by mass based on a mass of the zirconia composite ceramic, and in the basic structure, the inorganic oxide exists in at least one selected from a grain boundary between zirconia crystal grains adjoining each other and a grain boundary between a zirconia crystal grain and an aluminum oxide crystal grain adjoining, the manufacturing method including:

a preliminarily sintered body manufacturing step of molding a crystalline zirconium oxide powder containing the stabilizer and an aluminum oxide additive into a predetermined shape, and then preliminarily sintering the molded powder at 600 to 1200° C. to obtain a preliminarily sintered body composed of a microporous preliminarily sintered body having a relative density of 45 to 65%;

a sorption step of immersing the preliminarily sintered body obtained in the preliminarily sintered body manufacturing step in a sol in which fine particles of the inorganic oxide are dispersed in a dispersion medium and a concentration of the fine particles is 0.03 to 0.9% by mass based on a mass of the sol, to thereby sorb the fine particles of the inorganic oxide in pores of the microporous preliminarily sintered body; a drying step of removing the dispersion medium from the preliminarily sintered body subjected to the sorption step; and a final sintering step of sintering the preliminarily sintered body subjected to the drying step at a temperature of more than 1200° C. and 1800° C. or less to obtain the zirconia composite ceramic, wherein the predetermined shape in the preliminarily sintered body manufacturing step is conformed to a shape corresponding to a shape of a target article, or the preliminarily sintered body subjected to the drying step is processed into a shape corresponding to a shape of a target article after the drying step and before the final sintering step.

<8> The manufacturing method according to <7>, wherein, in the preliminarily sintered body manufacturing step, yttrium oxide is used as the stabilizer, in the sorption step, a sol in which silicon dioxide fine particles are dispersed is used as the sol, and in the final sintering step, the zirconia composite ceramic is obtained in which the zirconia crystal contained in the basic structure is a mixed crystal of yttrium oxide-solid dissolved tetragonal zirconia and yttrium oxide-solid dissolved cubic zirconia.

<9> The manufacturing method according to <7> or <8>, wherein biaxial flexure strength of the zirconia composite ceramic measured according to JIS T6526:2018 is 800 to 2000 MPa, and a contrast ratio is 0.5 to 0.8, the contrast ratio being an index of transparency, and being defined by the following expression:

$$\text{contrast ratio}=Yb/Yw$$

wherein Y means Y values obtained from a sample having a thickness of 1.0 mm±0.01 mm by spectral reflectance measurement using a spectrophotometer, and Yb and Yw represent the Y values measured with a background color black and a background color white, respectively.

Effects of the Invention

Finally sintering a specific composite material constituting a milling target part of a zirconia dental mill blank according to the present invention can provide a zirconia composite ceramic that is excellent in transparency and strength. Therefore, the zirconia dental mill blank according to the present invention can be used both for manufacturing a prosthesis for a front tooth, wherein aesthetics (transparency) is valued, and for manufacturing a prosthesis for a molar or a long-span bridge, required to have high strength. Moreover, since the above-mentioned specific composite material is based on a preliminarily sintered body of zirconia, the millability is also satisfactory in the same way as a conventional zirconia dental mill blank.

According to a method for manufacturing a zirconia dental mill blank according to the present invention, the zirconia dental mill blank according to the present invention can be manufactured, for example, by a very easy method involving using a preliminarily sintered body of a powder in which an aluminum oxide additive is blended into stabilized zirconia or partially stabilized zirconia, which has been widely used as milling target parts of conventional zirconia dental mill blanks, as a raw material, steeping this in a sol of an inorganic oxide, and then drying this. Moreover, since chemical reaction that requires complicated condition control or effort for preparating or complexing raw materials does not need to be utilized, a target material can be manufactured for a short period of time with good reproducibility efficiently.

According to a method for manufacturing a dental zirconia ceramic prosthesis according to the present invention or a method for manufacturing an article according to the present invention, a dental prosthesis or an article composed of a zirconia composite ceramic that has high transparency and high strength, and was difficult to obtain in the past can be easily and efficiently manufactured.

Preferred Mode for Carrying Out the Invention

A zirconia mill blank of the present disclosure has the greatest characteristic of the milling target part thereof being constituted of a specific composite material. This composite material is a composite material containing: a "matrix" including a "preliminarily sintered body of a crystalline zirconium oxide powder containing a stabilizer and an aluminum oxide additive"; and fine particles of an "inorganic oxide" excluding zirconium oxide, an inorganic oxide functioning as the stabilizer, and aluminum oxide (hereinafter also referred to as a "sorption inorganic oxide"). The zirconia composite ceramic (sintered body) characterized in that both strength and transparency are high out of the "trade-off relationship between strength and transparency" seen in a "sintered body of (partially) stabilized zirconia in which yttria is blended as a stabilizer" (hereinafter also referred to as a "conventional zirconia sintered body") can be obtained by finally sintering the composite material.

Although the mechanism in which the thus characterized zirconia composite ceramic (hereinafter also referred to as a "zirconia sintered body") of the present disclosure is obtained is not necessarily clear, from (1) the difference in structure between the composite material of the present disclosure and a preliminarily sintered body constituting the milling target part of a conventional common zirconia mill blank (hereinafter also referred to as a "conventional preliminarily sintered body"), (2) the comparison of the structure and physical properties of the zirconia sintered body of the present disclosure with the structure and physical properties of the conventional zirconia sintered body, (3) the relationship between the structure and physical properties in the conventional zirconia sintered body, and the like, it is conjectured that the mechanism is as follows.

That is, when the structure of the conventional preliminarily sintered body and (3) the relationship between the structure and physical properties in the conventional zirconia sintered body are first checked, the conventional preliminarily sintered body is a "preliminarily sintered body of (partially) stabilized zirconia containing the aluminum oxide additive", open pores derived from gaps between particles (namely holes opened outward) are formed in the process of the growth of necks with the formation of the necks by partially joining raw material powder particles in the preliminary sintering process. These open pores do not disappear, and many open pores remain in the preliminary sintering stage. Therefore, the conventional preliminarily sintered body has a microporous structure. In the final sintering, the pores shrink, and the grains grow in the process thereof. The finally obtained conventional zirconia sintered body has a "structure in which aluminum oxide grains are dispersed in a polycrystal structure formed by random dispersion and adjoining of tetragonal zirconia grains and cubic zirconia grains in which the stabilizer is solid dissolved at different concentrations (basic structure)". The balance between the strength and transparency of the conventional zirconia sintered body is determined basically depends on the existence ratio between tetragonal zirconia grains and cubic zirconia grains. That is, while tetragonal zirconia reduces the transparency due to generating birefringence, phase transition to a monoclinic crystal (with volume increase) due to stress (stress-induced phase transformation) applies compressive stress to crack ends to prevent cracks from extending in the cracking. Therefore, as the content ratio of tetragonal zirconia increases, the strength increases (for example, the flexural strength increases). On the other hand, while cubic zirconia can maintain the transparency highly due to not generating birefringence, an increase in this reduces tetragonal zirconia, which contributes relatively more to increase in strength, thereby reducing the strength.

Meanwhile, the matrix in the composite material of present disclosure is substantially the same as the conventional (microporous) preliminarily sintered body. However, the composite material of the present disclosure is different from the conventional preliminarily sintered body in that the sorption inorganic oxide is held in the pores of the matrix. It is confirmed by the analysis of the present inventors that while the zirconia sintered body of the present disclosure has the basic structure in the conventional zirconia sintered body, the sorption inorganic oxide exists in the grain boundary between zirconia crystal grains adjoining each other and/or the grain boundary between zirconia crystal grains and aluminum oxide crystal grains adjoining each other. As is clear from the comparison of Examples and Comparative Examples, described below, in the zirconia sintered body of the present disclosure, the contrast ratio, which is an index of transparency, is almost the same, but the biaxial flexural strength is significantly improved as compared with the sintered body of the matrix having the same composition and not complexed with the sorption inorganic oxide (corresponding to the conventional zirconia sintered body). According to the examination of the present inventors, it is confirmed that if a mixed powder of the (partially) stabilized zirconia powder, the aluminum oxide additive (powder), and the sorption inorganic oxide powder is finally sintered directly without using the composite material of the present disclosure, the biaxial flexural strength is improved, but the transparency decreases as compared with the sintered body of the matrix not containing the sorption inorganic oxide powder and having the same composition (corresponding to the conventional zirconia sintered body).

Accordingly, it is believed based on these facts that, in the zirconia sintered body of the present disclosure, the sorption inorganic oxide was sintered so that the sorption inorganic oxide existed in only the grain boundaries without forming (crystal) grains that reduce the transparency in the process of finally sintering the composite material, so that the sorption inorganic oxide performs the function of reducing breaking starting points at the time of stress loading without adversely affecting the transparency that the above-mentioned basic structure originally has (depending on the content of cubic crystals) or enhancing the interfacial strength especially in the cubic crystals to increase the strength. It is assumed that strength and transparency both increases beyond the above-mentioned trade-off relationship thereby. However, the present invention is not restricted at all by the above-mentioned assumed mechanism.

Hereinafter, the zirconia mill blank of the present disclosure and a manufacturing method therefor, a method for manufacturing a zirconia prosthesis of the present disclosure, and a method for manufacturing an article of the present disclosure will be described in detail.

The expression "x to y" using the numerical values x and y means "x or more and y or less" unless otherwise specified herein. When a unit is attached only to the numerical value y in such an expression, the unit is also applied to the numerical value x.

<Zirconia Mill Blank>

The zirconia mill blank of the present disclosure has a milling target part composed of a composite material, the composite material including: a matrix including a preliminarily sintered body of crystalline zirconium oxide powder containing a stabilizer and an aluminum oxide additive; and fine particles of a sorption inorganic oxide (namely an inorganic oxide excluding zirconium oxide, an inorganic oxide functioning as a stabilizer, and aluminum oxide). Other structures may be the same as the conventional zirconia mill blank.

In the zirconia mill blank of the present disclosure, the type and content ratio of the stabilizer and the content of the aluminum oxide additive contained in the preliminarily sintered body to be the matrix may be the same as those in the conventional preliminarily sintered body. For example, a preliminarily sintered body in which the total content of both is 0.005% by mass or more can be used. Among others, it is preferable to use a sintered body containing 5 to 14 parts by mass of yttria with respect to 100 parts by mass of zirconium oxide (0.027 to 0.076 mol with respect to 1 mol of zirconium oxide) as the stabilizer and containing 0.005 to 0.3 parts by mass of aluminum oxide with respect 100 parts by mass of zirconium oxide.

The preliminarily sintered body to be the matrix needs to be a microporous preliminarily sintered body having a relative density of 45 to 65% and having pores opened outward. Here, the relative density is calculated by finding the ratio of the actual density to the theoretical density {value calculated by the expression Relative density=(Actual density/Theoretical density)×100(%)}, and can be adjusted by controlling the preliminary sintering temperature and the preliminary sintering time. If the relative density is out of the above-mentioned range, it is difficult to obtain the composite material of the present disclosure. If preliminary sintering is performed so that the relative density is such a relative density, the preliminarily sintered body usually becomes a microporous preliminarily sintered body, having pores opened outward. The average pore diameter of these pores is usually in the range of 50 to 200 nm. Here, the average particle diameter means a median diameter calculated from the pore volume distribution in the pore diameter range of 5 nm to 250 μm obtained by mercury penetration, namely measurement with the mercury porosimeter.

The theoretical density varies depending on the content ratio and the type of the stabilizer and content ratio of the aluminum oxide additive, as these content ratios increase, the theoretical density tends to slightly decrease from 6.10 g/cm$^3$, namely the theoretical density of tetragonal zirconia. For example, the theoretical density of zirconia in which yttria and alumina are blended is shown in Table 1 of Patent Document 1 and therefore reproduced below as a reference.

TABLE 1

| $Y_2O_3$ content ratio (mol %) | $Al_2O_3$ content ratio (mol %) 0.000 | 0.050 | 0.080 |
|---|---|---|---|
| 3 | 6.095 | 6.093 | 6.092 |
| 3.5 | 6.086 | 6.084 | 6.083 |
| 4 | 6.080 | 6.078 | 6.077 |
| 4.1 | 6.080 | 6.078 | 6.077 |
| 4.5 | 6.072 | 6.070 | 6.070 |
| 5 | 6.062 | 6.060 | 6.060 |
| 5.5 | 6.052 | 6.050 | 6.050 |
| 6 | 6.043 | 6.041 | 6.041 |
| 6.5 | 6.033 | 6.032 | 6.031 |
| 7.4 | 6.019 | 6.017 | 6.017 |

The values in the table are theoretical densities. (g/cm$^3$)

As the preliminarily sintered body to be the matrix, a preliminarily sintered body newly manufactured according to a matrix manufacturing step in the method for manufacturing the zirconia mill blank described below may be used, but a preliminarily sintered body that is available as a milling target member of a conventional zirconia mill blank and has a known theoretical density (or composition) is measured for the density by Archimedes' method or the like to confirm the relative density thereof, and a preliminarily sintered body in which the value thereof is in the above-mentioned range may be used as the matrix as it is.

As the sorption inorganic oxide (namely inorganic oxide excluding zirconium oxide, an inorganic oxide functioning as the stabilizer and aluminum oxide), oxides having Group 4 elements and Group 14 elements are preferable. Silicon dioxide, titanium dioxide, tin oxide, and the like can be specifically used. Among these, it is preferable to use silicon dioxide from the viewpoint that the flexural strength of the zirconia sintered body of the present disclosure can be further increased.

In the composite material of the present disclosure, the fine particles of the sorption inorganic oxide need to be held in the pores of the microporous preliminarily sintered body to be a matrix. As mentioned above, if a powder composition in which the fine particles of the sorption inorganic oxide are blended in the crystalline zirconium oxide powder containing the stabilizer and the aluminum oxide additive is preliminarily sintered into a sintered body, it is difficult to obtain desired physical properties after the final sintering. The fine particles of the sorption inorganic oxide need to have a size that can be accommodated in the pores of the matrix necessarily to be held in the pores. The average primary particle diameter thereof is preferably smaller than the average pore diameter for which the microporous preliminarily sintered body to be the matrix is measured by mercury penetration. The fine particles preferably satisfy this condition, and have diameter of 2 to 100 nm, especially 10 to 30 nm.

The content ratio of the fine particles of the sorption inorganic oxide in the composite material of the present disclosure is preferably 0.09 to 10% by mass, and more preferably 0.09 to 1.5% by mass based on the total mass of the microporous preliminarily sintered body and the fine particles of the inorganic oxide.

<Method for Manufacturing Zirconia Mill Blank>

The method for manufacturing the zirconia mill blank of the present disclosure includes: a matrix manufacturing step of molding a crystalline zirconium oxide powder containing a stabilizer and an aluminum oxide additive into a predetermined shape, and then preliminarily sintering the molded powder at 600 to 1200° C. to obtain the above-mentioned matrix; a sorption step of immersing the matrix obtained in the matrix manufacturing step in a sol in which the fine particles of the sorption inorganic oxide are dispersed in a dispersion medium and the concentration of the fine particles is 0.03 to 0.9% by mass based on the mass of the sol, to thereby sorb the fine particles of the sorption inorganic oxide in the pores of the microporous preliminarily sintered body constituting the matrix; and a drying step of removing the above-mentioned dispersion medium from the matrix subjected to the sorption step. Hereinafter, these steps will be described in detail.

[Matrix Manufacturing Step]

In the matrix manufacturing step, the crystalline zirconium oxide powder containing the stabilizer and the aluminum oxide additive (hereinafter also referred to as a "raw material powder") is molded into the predetermined shape, and then preliminarily sintered at 600 to 1200° C. to manufacture the matrix including the preliminary sintered body of the crystalline zirconium oxide powder.

(Raw Material Powder)

As the raw material powder, a crystalline zirconium oxide powder containing the stabilizer and aluminum oxide as the additive is used.

The stabilizer for the zirconium oxide powder such as yttrium oxide, calcium oxide, magnesium oxide, cerium oxide, or erbium oxide used as the stabilizer for zirconium oxide until now can be used without limitation. Among those, yttrium oxide is preferable. The content of yttrium oxide is preferably 5 to 14 parts by mass with respect to 100 parts by mass of zirconium oxide (0.027 to 0.076 mol with respect to 1 mol of zirconium oxide) from the viewpoint of obtaining stabilized zirconia or partially stabilized zirconia after the sintering.

Aluminum oxide is contained in the raw material powder as a sintering aid for zirconium oxide, and the content thereof is preferably 0.005 to 0.3 parts by mass with respect to 100 parts by mass of zirconium oxide. When the content of aluminum oxide is 0.005 parts by mass or more, an effect as the sintering aid tends to be fully obtained. When the content is 0.3 parts by mass or more, a decrease in translucency due to the refractive index difference from zirconium oxide tends to be able to be suppressed.

As long as the raw material powder is easily handled as a powder, the raw material powder is not particularly limited. Since the phase transformation of the oxide crystals hardly occur, and the grain growth does not proceed excessively by sintering, the average crystallite diameter is preferably 0.001 to 50 μm, and more preferably 0.003 to 20 μm.

The raw material powder may contain a pigment. The pigment is not particularly limited, well-known pigments can be freely used in combination, and, for example, erbium oxide, cobalt oxide, iron oxide, and the like can be used. A substance that is colored after sintering even though the substance is white before the sintering can also be used as the pigment.

The raw material powder can contain a binder, a fine filler, a light-shielding agent, a fluorescent agent, and the like as other components. It can be appropriately selected depending on the method for molding the sintered body, and the like whether the binder component is added or not. If the binder component is added, for example, an acrylic binder, an olefinic binder, a wax, or the like can be used.

(Molding)

In the matrix manufacturing step, a compression-molded body or a green body in the predetermined shape is obtained using the above-described raw material powder. The molding method may be the same as the conventional method involving obtaining a molded body for a mill blank before sintering or before calcination using a conventional raw material powder. Methods such as press molding, extrusion, injection molding, cast molding, tape molding, molding by layering shaping, molding by powder shaping, and molding by optical shaping known as powder molding methods or green body molding methods can be used without particular limitation. The matrix may be subjected to multistage molding. For example, the raw material powder is subjected to uniaxial press molding, and the molded body may then be further subjected to CIP (cold isostatic pressing) treatment. A plurality of mixed powders may be layered and molded.

The shape of the compression-molded body or the green body obtained by the molding only has to be appropriately determined depending on the shape of the target mill blank, but a discoidal article (disk type) or a cuboidal or almost cuboidal article (block type) is usually common.

(Preliminary Sintering)

In the matrix manufacturing step, the compression-molded body or the green body obtained by the molding is sintered at a temperature lower than that in final sintering treatment for dewaxing treatment and calcination treatment to obtain the matrix. Here, the dewaxing treatment means treatment for removing water, the solvent, the binder, and the like contained in the compression-molded body or the green body obtained by the molding by volatilization or decomposition. The calcination treatment means treatment for increasing the strength of the obtained microporous preliminarily sintered body to such strength that the microporous preliminarily sintered body is easily handled and easily processed while causing a molecule or atom diffusion (adhesion or fusion) phenomenon on the surfaces of the powder particles of the metal oxide by heating for change into a polycrystal. The preliminary sintering temperature is usually 600 to 1200° C. If the preliminary sintering temperature is lower than 600° C., the strength that enables maintain the shape in the sorption step may not be obtained. If the preliminary sintering temperature is higher than 1200° C., the density of the matrix increases, the sol cannot be fully infiltrated, and the strength may not be high.

As the method for dewaxing and/or calcination treatment, a method known conventionally can be used without particular limitation, and the method for dewaxing and/or calcination treatment may be performed continuously or in multiple stages. The method for dewaxing and/or calcination treatment is preferably performed in the air atmosphere containing oxygen to remove organic matter efficiently. The dewaxing and/or the calcination treatment can be successively performed by a method, for example, SPS (spark plasma sintering), HP (hot press), or the like using a device that is the same as in the molding treatment, which is a previous step.

[Sorption Step]

In the sorption step, the matrix obtained in the matrix manufacturing step is immersed in a sol in which the fine particles of the sorption inorganic oxide are dispersed in a dispersion medium and the concentration of the fine particles is 0.03 to 0.9% by mass based on the mass of the above-mentioned sol (hereinafter also referred to as a "sorption inorganic oxide-dispersed sol"), to thereby sorb the fine particles of the sorption inorganic oxide in the pores of the microporous preliminarily sintered body constituting the matrix.

(Sorption Inorganic Oxide-Dispersed Sol)

As long as the sorption inorganic oxide-dispersed sol is a liquid in which one or more types of oxide particles including the inorganic oxide excluding zirconium oxide, the stabilizer for zirconium oxide, and aluminum oxide are dispersed, the sorption inorganic oxide-dispersed sol is not particularly limited. The sorption oxide-dispersed sol in which the oxide particles are dispersed in the dispersion medium having a viscosity of 0.05 Pa·s or less is preferable, and the sorption inorganic oxide-dispersed sol using water or an alcohol for the dispersion medium is particularly preferable from the viewpoint of impregnating the pores of the microporous preliminarily sintered body constituting the matrix.

In the sorption inorganic oxide-dispersed sol, the concentration of an oxide contained as a main ingredient among oxides dispersed in the sorption inorganic oxide-dispersed sol is preferably 0.03 to 0.9% by mass, and more preferably 0.05 to 0.5% by mass. If the concentration of the oxide contained as the main ingredient is less than 0.03% by mass, enough strength for the dental sintered body may not be obtained after the final sintering. If the concentration is more than 0.9% by mass, the transparency may decrease due to the refractive index difference from zirconium oxide, the strength enough for a dental sintered body may not be obtained due to low strength of the oxide, and the occurrence of the aggregation of the oxide, or the like may prevent the impregnation of fine pores between the primary particles. Here, the main ingredient means a substance contained at 80% by mass or more with respect to the total mass of the oxide dispersed in the sorption inorganic oxide-dispersed sol.

As long as the oxide contained in the sorption inorganic oxide-dispersed sol as the main ingredient is an oxide other than zirconium oxide, the stabilizer for zirconium oxide, and aluminum oxide, the oxide can be used without particular limitation, but the oxide is preferably an oxide having a Group 4 element and a Group 14 element. Specific examples of the oxide include silicon dioxide, titanium dioxide, and tin oxide, but the oxide is preferably silicon dioxide from the viewpoint of further improving the flexural strength.

The oxide fine particles contained in the sorption inorganic oxide-dispersed sol as the main ingredient need to have a size that can be accommodated in the pores of the matrix necessarily. The average primary particle diameter thereof is preferably smaller than the average pore diameter for which the microporous preliminarily sintered body to be the matrix is measured by mercury penetration. The fine particles preferably satisfy this condition, and have a diameter of 2 to 100 nm, especially 10 to 30 nm. When the average primary particle diameter of the oxide fine particles is 2 nm or more, a highly dispersed state are easily maintained, and the aggregation tends to be suppressed. When the average primary particle diameter is 100 nm or less, the inside of the microporous preliminarily sintered body can be impregnated with the oxide fine particles, and enough strength for the dental sintered body tends to be obtained.

The average primary particle diameter of the oxide fine particles is a value determined by nitrogen adsorption. That is, the average primary particle diameter means an average particle diameter calculated based on the specific surface area determined by nitrogen adsorption using a dried powder obtained by drying the medium and the density of the inorganic oxide.

The sorption inorganic oxide-dispersed sol may contain additives such as a binder, a dispersant, an emulsifier, and a pH adjustor to prevent the sedimentation of the oxide particles. The additives may be used alone or in combination two or more.

Examples of the binder include polyvinyl alcohol, polyvinylpyrrolidone, methylcellulose, carboxymethyl cellulose, polyacrylic acid, acrylic binders, wax binders, polyvinyl butyral, polymethyl methacrylate, ethyl cellulose, polyethylene glycol, glycerin, propylene glycol, and dibutyl phthalate.

Examples of the dispersant include ammonium polycarboxylate, ammonium polyacrylate, an acrylic copolymer resin, an acrylic acid ester copolymer, polyacrylic acid, bentonite, carboxymethyl cellulose, anionic surfactants, nonionic surfactants, olein glyceride, amine surfactants, and oligosaccharide alcohols.

Examples of the emulsifier include alkyl ether, phenyl ether, sorbitan derivatives, and ammonium salts.

Examples of the pH adjustor include ammonia, ammonium salts, alkali metal salts, and alkaline-earth metal salts.

The sorption inorganic oxide-dispersed sol may contain a component that colors zirconia or imparts fluorescence. Examples of the coloring component include iron ions and cobalt ions. Examples of the fluorescence-imparting component include bismuth ions and neodymium ions.

(Immersion)

In the sorption step, the matrix obtained in the matrix manufacturing step is immersed in the sorption inorganic oxide-dispersed sol, and the fine particles of the sorption inorganic oxide are sorbed in the pores of the microporous preliminarily sintered body constituting the matrix. As long as the immersion method is a method for infiltrating the sorption inorganic oxide-dispersed sol into the pores of the microporous preliminarily sintered body constituting the matrix, the immersion method is not particularly limited, and may be performed under reduced pressure, under normal pressure, or under pressure. As long as the immersion time is time for which the sorption inorganic oxide-dispersed sol is fully infiltrated into the pores of the microporous preliminarily sintered body constituting the matrix, the immersion time can also be freely selected. As long as the immersion temperature is temperature at which the sorption inorganic oxide-dispersed sol is fully infiltrated into the pores of the microporous preliminarily sintered body constituting the matrix, the immersion temperature can also be freely selected. However, a temperature lower than the boiling point of the dispersion medium of the sorption inorganic oxide-dispersed sol is preferable.

[Drying Step]

In the drying step, the above-mentioned dispersion medium is removed from the matrix subjected to the sorption step. As long as the drying method is the method that enables removing the dispersion medium of the sorption inorganic oxide-dispersed sol, the drying method is not particularly limited, but it is preferable to adopt reduced pressure drying and/or heating drying from the viewpoint that the solvent can be easily removed while the shape of the matrix is maintained. Here, the reduced pressure drying is a method for removing the dispersion medium, for example, under a reduced pressure of 800 hPa or less, and the heating drying is a method for removing the dispersion medium at temperature that is room temperature or higher. The dispersion medium can be removed (dried) at temperature lower than the boiling point of the dispersion medium by heating under reduced pressure.

Calcination treatment may be performed with the drying treatment again. For example, the drying treatment and the calcination treatment may be performed at the same time or in multiple stages.

<Method for Manufacturing Zirconia Prosthesis>

In a method for manufacturing a zirconia prosthesis of the present disclosure, a zirconia prosthesis composed of a zirconia composite ceramic is manufactured. Here, the zirconia composite ceramic has, as a basic structure, a structure in which aluminum oxide crystal grains as an additive are dispersed in a polycrystal structure formed by bonding of the same or different types of zirconia crystals in which a stabilizer is solid dissolved, and further includes a sorption inorganic oxide, the content ratio of the sorption inorganic oxide contained in the zirconia composite ceramic is 0.09 to 10% by mass based on the mass of the zirconia composite ceramic, and in the above-mentioned basic structure, the sorption inorganic oxide exists in at least one selected from the grain boundary between zirconia crystal grains adjoining each other and the grain boundary between a zirconia crystal grain and an aluminum oxide crystal grain adjoining. The method for manufacturing a zirconia prosthesis of the present disclosure includes a milling step of milling a milling target part of the zirconia dental mill blank of the present disclosure using a CAD/CAM system to obtain a semifinished product having a shape corresponding to the target dental prosthesis and composed of the above-mentioned composite material and a final sintering step of sintering the semifinished product at a temperature of more than 1200° C. and 1800° C. or less to change the above-mentioned composite material into the above-mentioned zirconia composite ceramic. Hereinafter, the zirconia prosthesis and these steps of the present disclosure will be described in detail.

[Zirconia Prosthesis]

The zirconia prosthesis of the present disclosure may be the same as a conventional zirconia prosthesis except that the zirconia prosthesis is composed of the zirconia composite ceramic.

The content ratio of the sorption inorganic oxide contained in the zirconia composite ceramics needs to be 0.09 to 10% by mass, and is more preferably 0.09 to 1.5% by mass based on the mass of the zirconia composite ceramic in the zirconia prosthesis of the present disclosure.

The zirconia prosthesis of the present disclosure can be used both for manufacturing a prosthesis for a front tooth, wherein aesthetics (transparency) is valued, and for manufacturing a prosthesis for a molar or a long-span bridge, required to have high strength as the zirconia composite ceramic that is excellent in transparency and strength. Therefore, the biaxial flexure strength is preferably 800 to 2000 MPa, and more preferably 1100 to 2500 MPa. The contrast ratio (Yb/Yw), which is an index of transparency, is preferably 0.5 to 0.8, and more preferably 0.5 to 0.7. If the biaxial flexure strength is less than 800 MPa, the prosthesis such as a long-span bridge, required to have high strength, may be broken. If the biaxial flexure strength is more than 2000 MPa, the opposed teeth and the like may be damaged due to too high strength. If the abutment tooth is much discolored, or the material is a metal, the prosthesis having a contrast ratio (Yb/Yw) of less than 0.5 may not appear aesthetic under the influence of the color of the abutment tooth in wearing the prosthesis. The prosthesis having a contrast ratio (Yb/Yw) of more than 0.8 is opaque in a line with natural teeth, and may not appear aesthetic.

The biaxial flexure strength is measured according to JIS T6526:2018. The contrast ratio (Yb/Yw) is a value that is an index of the ceramic transparency, and is determined as follows using a spectrophotometer or a differential colorimeter. That is, both sides of a ceramic (a little thicker than 1 mm) are polished to a thickness of 1.0 mm±0.01 mm using wet abrasive papers #800, #1500, and #3000 sequentially and then mirror-polished using SUPER STAR V (produced by NIPPON SHIKAKOGYOSHA Co., Ltd.), which is an abrasive material for porcelain hybrid resin zirconia, to manufacture a test piece to be a measurement sample. Then, the test piece is measured for the spectral reflectance with the background color black and the background color white using a spectrophotometer or a differential colorimeter to determine Y values in the black background (Yb) and a Y value in the white background (Yw). The contrast ratio (Yb/Yw) can be calculated by dividing Yb by Yw. As the value of the contrast ratio decreases, the transparency increases.

[Milling Step]

In the milling step, the milling target part of the zirconia mill blank of the present disclosure is milled using a CAD/CAM system to obtain a semifinished product having a shape corresponding to the shape of a target dental prosthesis and composed of the above-mentioned composite material. Since the zirconia mill blank needs to be attached to a CAM apparatus in milling, the shape of the mill blank is preferably a (solid) block shape molded into a cuboidal or columnar shape or a (solid) disk shape formed into a platy shape or a discoid shape. The mill blank may have a holding part that enable this to be attached to a milling machine as necessary.

The obtained semifinished product is milled using a CAD/CAM system. Then, the form may be further modified using a technical engine or the like, or the surface may be polished. The tone may be adjusted using a permeable coloring agent, transparentizing liquid, or the like as necessary.

[Final Sintering Step]

In the final sintering step, the semifinished product obtained in the milling step is sintered at a temperature of more than 1200° C. and 1800° C. or less to change the above-mentioned composite material into the zirconia composite ceramic. The final sintering is preferably performed at a temperature of 1400 to 600° C. If the final sintering temperature is 1200° C. or lower, enough sintered density, translucency, and strength may not be obtained. If the sintering temperature is higher than 1800° C., enough strength may not be obtained due to excessive grain growth of zirconium oxide.

As the sintering method, a conventionally known method can be used without particular limitation, and the holding time at the sintering temperature is preferably 30 minutes to 4 hours.

After the final sintering step, a form modification step using a diamond bar or the like or a polishing step using diamond paste or the like may be performed. Furthermore, porcelain or the like may be baked on the surface of the zirconia prosthesis of the present disclosure to make the tone more similar to a natural tooth and aesthetic.

<Method for Manufacturing Article Composed of Zirconia Composite Ceramic>

A method for manufacturing an article of the present disclosure is a method for manufacturing an article composed of the above-described zirconia composite ceramic, including: a preliminarily sintered body manufacturing step of molding a crystalline zirconium oxide powder containing a stabilizer and an aluminum oxide additive into a predetermined shape, and then preliminarily sintering the molded powder at 600 to 1200° C. to obtain a preliminarily sintered body composed of a microporous preliminarily sintered body having a relative density of 45 to 65%; a sorption step of immersing the preliminarily sintered body obtained in the preliminarily sintered body manufacturing step in a sol in which fine particles of a sorption inorganic oxide are dispersed in a dispersion medium and the concentration of the fine particles is 0.03 to 0.9% by mass based on the mass of the sol, to thereby sorb the fine particles of the sorption inorganic oxide in the pores of the preliminarily sintered body; a drying step of removing the dispersion medium from the preliminarily sintered body subjected to the sorption step; and a final sintering step of sintering the preliminarily sintered body subjected to the drying step at a temperature of more than 1200° C. and 1800° C. or less to obtain the zirconia composite ceramic, wherein the predetermined shape in the preliminarily sintered body manufacturing step is conformed to the shape corresponding to the shape of a target article, or the preliminarily sintered body subjected to the drying step is processed into the shape corresponding to the shape of a target article after the drying step and before the final sintering step.

The method for processing the preliminarily sintered body into the shape corresponding to the shape of the target article may be the same as the processing method used for conventional ceramics except that the preliminarily sintered body obtained after the preliminarily sintered body manufacturing step or the drying step is used. As the processing method, cutting, grinding, hole making, or the like can be performed without particular limitation. Milling using an apparatus as represented by a CAD/CAM system is preferable from the viewpoint that the preliminarily sintered body can processed with higher accuracy.

The relative density of the preliminarily sintered body composed of a microporous preliminarily sintered body is preferably 45 to 65%. If the relative density is less than 45%, the transparency and the strength of the final sintered body may be not obtained, and the shape may not be able to be maintained in processing. If the relative density is more than 65%, the strength is high, and the processing may be difficult.

In the method for manufacturing the article of the present disclosure, in the preliminarily sintered body manufacturing step, the stabilizer to be used is preferably yttrium oxide, and in the sorption step, the sol to be used is preferably a sol in which silicon dioxide fine particles are dispersed. In the final sintering step, the zirconia composite ceramic obtained preferably has zirconia crystals contained in the above-mentioned basic structure that is a mixed crystal of yttrium oxide-solid dissolved tetragonal zirconia and yttrium oxide-solid dissolved cubic zirconia.

Furthermore, in the method manufacturing for the article of the present disclosure, the biaxial flexure strength of the obtained article is preferably 800 to 2000 MPa, and the contrast ratio (Yb/Yw) is preferably 0.5 to 0.8.

EXAMPLES

The zirconia mill blank of the present disclosure has the main characteristic with respect to a composite material (preliminarily sintered body) constituting a milling target part, and a manufacturing method therefor also has the main characteristic in that the composite material is manufactured. A method for manufacturing a zirconia prosthesis of the present disclosure and a method for manufacturing an article of the present disclosure both have the main characteristic in that the composite material is finally sintered to obtain a zirconia composite ceramic (zirconia sintered body) having a specific structure. Then, the present invention will be specifically described with respect to the method for manufacturing the article of the present disclosure including a preliminarily sintered body manufacturing step of obtaining the composite material and a final sintering step of obtaining the zirconia sintered body by showing Examples and Comparative Examples. However, the present invention is not limited to these Examples.

First, raw materials used in Examples and Comparative Examples, abbreviations and codes thereof, and the like will be described.

[Raw Material Powder]

ZpexSmile: Produced by Tosoh Corporation, zirconium oxide (aluminum oxide content ratio: 0.05% by mass, yttrium oxide content ratio: 9.3% by mass, theoretical density: 6.050 g/cm$^3$)

Zpex4: Produced by Tosoh Corporation, zirconium oxide (aluminum oxide content ratio: 0.05% by mass, yttrium oxide content ratio: 6.9% by mass, theoretical density: 6.078 g/cm$^3$)

Zpex: Produced by Tosoh Corporation, zirconium oxide (aluminum oxide content ratio: 0.05% by mass, yttrium oxide content ratio: 5.3% by mass, theoretical density: 6.093 g/cm$^3$)

TZ-3Y-SE: Produced by Tosoh Corporation, zirconium oxide (aluminum oxide content ratio: 0.26% by mass, yttrium oxide content ratio: 5.2% by mass, theoretical density: 6.085 g/cm$^3$)

TZ-8YSB: Produced by Tosoh Corporation, zirconium oxide (aluminum oxide content ratio: 0.005% by mass or less, yttrium oxide content ratio: 13.74% by mass, theoretical density: 6.011 g/cm$^3$)

[Sorption Inorganic Oxide]

LUDOX-LS: Produced by Nissan Chemical Corporation, silicon dioxide sol (silicon dioxide content ratio: 30% by mass, average primary particle diameter: 12 nm, dispersion medium: water)

LUDOX-AS30: Produced by Nissan Chemical Corporation, silicon dioxide sol (silicon dioxide content ratio: 30% by mass, average primary particle diameter: 12 nm, dispersion medium: water)

LUDOX-SM: Produced by Nissan Chemical Corporation, silicon dioxide sol (silicon dioxide content ratio: 30% by mass, average primary particle diameter: 7 nm, dispersion medium: water)

$TiO_2$ sol: Produced by Osaka Gas Chemicals Co., Ltd., titanium dioxide sol (titanium dioxide content ratio: 5% by mass, average primary particle diameter: 3 nm, dispersion medium: water)

Ceramace S-8: Produced by Taki Chemical Co., Ltd., tin oxide sol (tin oxide content ratio: 8% by mass, average primary particle diameter: 2 nm or less, dispersion medium: water)

MT-10: Produced by Tokuyama Corporation, silica fine powder (average primary particle diameter: 15 nm)

Example 1

(1) Matrix Manufacturing Step and Evaluation of Obtained Microporous Preliminarily Sintered Body (Matrix)

ZpexSmile (1.5 g) was subjected to uniaxial pressing using a mold for the press having a diameter of 20 mm at a maximum load of 200 MPa to obtain a discoidal molded body (thickness: 1.45 mm). Then, the molded body was preliminarily sintered using a ring furnace under conditions of 1000° C. and 30 minutes to obtain a microporous preliminarily sintered body (thickness: 1.45 mm) to be a matrix. When the density was calculated from the mass and volume of the obtained discoidal microporous preliminarily sintered body, and the relative density was found by dividing this by the theory sintered density, the relative density was 49.8%.

A discoidal microporous preliminarily sintered body having a thickness of 5 mm was manufactured in the same way separately from this except that the amount of the powder used was changed into 6.5 g and then cut into a prismal shape of 5 mm×5 mm×5 mm to manufacture a sample for measuring the average pore diameter. When the average pore diameter was measured using this sample, the average pore diameter was 103 nm. The average pore diameter was measured at a mercury surface tension of 480 erg/cm$^2$ (=480 mJ/m$^2$), a contact angle of 140°, a discharge contact angle of 140°, a pressure of 0 to 50000 psia (=0 to 344.75 MPa) using a fully automatic multifunctional mercury porosimeter (manufactured by Anton Paar GmbH, "POREMASTER").

(2) Sorption Step and Drying Step, and Evaluation of Obtained Composite Material LUDOX-LS (0.03 g) and ion-exchanged water (10 mL) were mixed to prepare a sorption inorganic oxide-dispersed sol. The matrix obtained in the matrix manufacturing step was immersed in the prepared sorption inorganic oxide-dispersed sol at normal temperature and normal pressure (25° C. and 1 atmosphere), left to stand for 1 hour, then taken out of the sorption inorganic oxide-dispersed sol, and dried on a hot stirrer set at 120° C. for 20 minutes to obtain a composite material. When a composite material manufactured separately in the same way was analyzed with a field emission electron probe microanalyzer (FE-EPMA), and the content ratio of the sorption inorganic oxide (that is silicon dioxide in the present Example) was determined based on the results, the content ratio was 0.24% by mass.

(3) Final Sintering Step and Evaluation of Obtained Finally Sintered Body (Zirconia Composite Ceramic)

The obtained composite material was sintered in an electric furnace under the conditions of 1450° C. and 2 hours to obtain a finally sintered body. When the biaxial flexure strength and transparency of the obtained finally sintered body were evaluated as follows, the biaxial flexure strength was 1235 MPa, and the contrast ratio (Yb/Yw) was 0.648.

[Evaluation of Biaxial Flexure Strength]

Measurement was performed according to JIS T6526: 2018 under the conditions of a crosshead speed of 1.0 mm/min, a support circle diameter of 10 mm, and an indenter diameter of 1.4 mm using a tester manufactured by SHIMADZU CORPORATION. The biaxial flexure strength was calculated by the following expression.

$$\delta=-0.2387\times P\times(X-Y)/b^2$$

$$X=(1+\nu)\times\ln[(r2/r3)^2]+[(1-\nu)/2]\times(r2/r3)^2$$

$$Y=(1+\nu)\times[1+\{\ln(r1/r3)^2\}]+(1-\nu)\times(r1/r3)^2$$

δ [MPa]: Biaxial flexure strength
P [N]: Test force
b [mm]: Test piece thickness
ν: Poisson's ratio (0.31)
r1 [mm]: Supporting circle radius
r2 [mm]: Indenter radius
r3 [mm]: Test piece radius

[Transparency Evaluation]

The finally sintered body was polished to a thickness of 1.0 mm using wet abrasive papers #800, #1500, and #3000, and both sides were then mirror-polished using SUPER STAR V (produced by NIPPON SHIKAKOGYOSHA Co., Ltd.), which was an abrasive material for porcelain hybrid resin zirconia, and the finally sintered body was used as a sample for evaluating the transparency. The above-mentioned sample was measured for the spectral reflectances with the background color black and the background color white using a spectrophotometer (manufactured by Tokyo Denshoku Co., Ltd., spectrocolorimeter "TC-1800MKII"). The transparency was evaluated using the contrast ratio (Yb/Yw), calculated by dividing the Y value in the black background (Yb) by the Y value in the white background (Yw). As Yb/Yw decreases, the transparency increases.

Examples 2 to 14 and Comparative Examples 1 to 3

Microporous preliminarily sintered bodies (matrices), composite materials, and finally sintered bodies (zirconia composite ceramics) were manufactured in the same way as in Example 1 except that the type of the raw material powder, the type and blended amount of the sorption inorganic oxide-dispersed sol, the preliminarily sintering temperature, and the final sintering temperature were changed as shown in Table 2 and Table 3 and evaluated in the same way as in Example 1. Table 5 shows the evaluation results. The sign "↑" in Table 2 and Table 3" means "the same as above".

Comparative Example 4

Comparative Example 4 is an example in which a sorption inorganic oxide powder was attached to the surface of a microporous preliminarily sintered body without sorbing the sorption inorganic oxide-dispersed sol. In Comparative Example 4, ZpexSmile (1.5 g) was first subjected to uniaxial pressing using a mold for pressing having a diameter of 20 mm at a maximum load of 200 MPa to obtain a discoidal molded body (thickness: 1.45 mm). Then, the molded body was preliminarily sintered using a ring furnace under the conditions of 1000° C. and 30 minutes to obtain a microporous preliminarily sintered body (thickness: 1.45 mm). Table 5 shows the evaluation results of the obtained microporous preliminarily sintered body. Then, MT-10 (0.01 g) was placed on the obtained microporous preliminarily sintered body, and the preliminarily sintered body was sintered in an electric furnace under conditions of 1450° C. and 2 hours to obtain a finally sintered body. Table 5 shows the evaluation results of the obtained finally sintered body.

Reference Examples 1 to 4 (Examples in which Conventional Zirconia Sintered Bodies were Manufactured Using Conventional Preliminarily Sintered Bodies)

In Reference Example 1, the finally sintered body was obtained in the same way as in Example 1 except that the preliminarily sintered body was immersed using ion-exchanged water (10 mL), not containing a sorption inorganic oxide, instead of the sorption inorganic oxide-dispersed sol. In Reference Example 2 to 4, microporous preliminarily sintered bodies were obtained in the same way as in Reference Example 1 except that the type of the raw material powder was changed as shown in Table 4, and these were finally sintered as they are (without performing the sorption step) to obtain finally sintered bodies. The sign "t" in Table 4" means "the same as above". With respect to the compositions of the raw material powders, the preliminary sintering conditions, and the final sintering conditions, Reference Example 1 is the same as Example 1, and Reference Examples 2-4 are the same as Examples 10-12, respectively. Table 5 shows the evaluation results of the obtained microporous preliminarily sintered bodies (matrices) and the finally sintered bodies.

TABLE 2

| Example No. | Raw material powder Type | Raw material powder Blended amount [g] | Sorption inorganic oxide-dispersed sol* Type | Sorption inorganic oxide-dispersed sol* Blended amount [g] | Preliminary sintering temperature [° C.] | Final sintering temperature [° C.] |
|---|---|---|---|---|---|---|
| 1 | ZpexSmile | 1.5 | LUDOX-LS | 0.03 | 1000 | 1450 |
| 2 | ↑ | ↑ | ↑ | 0.01 | ↑ | ↑ |
| 3 | ↑ | ↑ | ↑ | 0.09 | ↑ | ↑ |
| 4 | ↑ | ↑ | ↑ | 0.15 | ↑ | ↑ |
| 5 | ↑ | ↑ | ↑ | 0.30 | ↑ | ↑ |
| 6 | ↑ | ↑ | LUDOX-AS30 | 0.03 | ↑ | ↑ |
| 7 | ↑ | ↑ | ↑ | 0.09 | ↑ | ↑ |
| 8 | ↑ | ↑ | LUDOX-SM | 0.03 | ↑ | ↑ |
| 9 | ↑ | ↑ | LUDOX-LS | ↑ | 1100 | ↑ |
| 10 | Zpex4 | ↑ | ↑ | ↑ | 1000 | ↑ |
| 11 | Zpex | ↑ | ↑ | ↑ | ↑ | ↑ |
| 12 | TZ-3Y-SE | ↑ | ↑ | ↑ | ↑ | ↑ |
| 13 | ZpexSmile | ↑ | TiO2 sol | 0.52 | ↑ | ↑ |
| 14 | ↑ | ↑ | Ceramace S-8 | 0.14 | ↑ | ↑ |

*The sorption inorganic oxide-dispersed sols used in all the Examples were prepared by mixing the raw material sols shown in the type column in the amounts shown in the blended amount column into 10 ml of ion-exchanged water.

TABLE 3

| Comparative Example No. | Raw material powder Type | Raw material powder Blended amount [g] | Sorption inorganic oxide Type | Sorption inorganic oxide Blended amount [g] | Preliminary sintering temperature [° C.] | Final sintering temperature [° C.] |
|---|---|---|---|---|---|---|
| 1 | ZpexSmile | 1.5 | LUDOX-LS*[1] | 0.03 | 800 | 1050 |
| 2 | ↑ | ↑ | ↑ | 0.03 | 1300 | 1450 |
| 3 | TZ-8YSB | ↑ | ↑ | 0.03 | 1000 | ↑ |
| 4 | ZpexSmile | ↑ | MT-10*[2] | 0.01 | ↑ | ↑ |

*[1]: In Comparative Examples 1 to 3, the sorption step and the drying step were performed using the sorption inorganic oxide-dispersed sols prepared by mixing the raw material sols shown in the type column in the amounts shown in the blended amount column into 10 ml of ion-exchanged water.
*[2]: In Comparative Example 4, the powder shown in the type column was used as it was without performing the sorption step or the drying step.

TABLE 4

| Reference Example No. | Raw material powder Type | Raw material powder Blended amount [g] | Preliminary sintering temperature [° C.] | Final sintering temperature [° C.] |
|---|---|---|---|---|
| 1 | ZpexSmile | 1.5 | 1000 | 1450 |
| 2 | Zpex4 | ↑ | ↑ | ↑ |
| 3 | Zpex | ↑ | ↑ | ↑ |
| 4 | TZ-3Y-SE | ↑ | ↑ | ↑ |

TABLE 5

| | | Evaluation result of microporous preliminarily sintered body: Average pore diameter [nm] | Evaluation result of microporous preliminarily sintered body: Relative density [%] | Content ratio of sorption inorganic oxide in composite material [% by mass] | Evaluation result of finally sintered body: Biaxial flexural strength [MPa] | Evaluation result of finally sintered body: Contrast ratio |
|---|---|---|---|---|---|---|
| Example | 1 | 103 | 49.8 | 0.24 | 1235 | 0.648 |
| | 2 | 103 | 49.1 | 0.08 | 955 | 0.650 |
| | 3 | 103 | 50.3 | 0.60 | 1123 | 0.649 |
| | 4 | 103 | 51.2 | 0.74 | 1103 | 0.693 |
| | 5 | 103 | 51.6 | 1.53 | 1007 | 0.755 |
| | 6 | 103 | 49.9 | 0.20 | 1007 | 0.667 |
| | 7 | 103 | 50.5 | 0.52 | 1119 | 0.716 |

TABLE 5-continued

| | | Evaluation result of microporous preliminarily sintered body: Average pore diameter [nm] | Evaluation result of microporous preliminarily sintered body: Relative density [%] | Content ratio of sorption inorganic oxide in composite material [% by mass] | Evaluation result of finally sintered body: Biaxial flexural strength [MPa] | Evaluation result of finally sintered body: Contrast ratio |
|---|---|---|---|---|---|---|
| | 8 | 103 | 49.8 | 0.16 | 1017 | 0.760 |
| | 9 | 91 | 54.5 | 0.64 | 1218 | 0.644 |
| | 10 | 78 | 52.6 | 0.30 | 1296 | 0.701 |
| | 11 | 60 | 52.5 | 0.25 | 1373 | 0.729 |
| | 12 | 59 | 52.6 | 0.23 | 1388 | 0.801 |
| | 13 | 103 | 51.3 | 0.61 | 986 | 0.657 |
| | 14 | 103 | 50.2 | 0.33 | 1045 | 0.664 |
| Comparative Example | 1 | 210 | 40.3 | 0.28 | 47 | 0.998 |
| | 2 | 31 | 70.1 | 0.04 | 911 | 0.661 |
| | 3 | 101 | 48.2 | 0.23 | 541 | 0.986 |
| | 4 | 103 | 49.6 | 0.62 | 837 | 0.821 |
| Reference Example | 1 | 103 | 49.6 | — | 905 | 0.658 |
| | 2 | 78 | 52.6 | — | 1118 | 0.693 |
| | 3 | 60 | 52.5 | — | 1214 | 0.725 |
| | 4 | 59 | 52.6 | — | 1237 | 0.799 |

As shown in Table 5, in Examples 1 to 14, in which the dental mill blanks satisfying the conditions prescribed in the present disclosure were manufactured, the sintered bodies that were highly dense and had high transparency and high strength were obtained. Meanwhile, in Comparative Example 1, in which the relative density of the microporous preliminarily sintered body was less than the lower limit prescribed in the present disclosure, enough density was not obtained after the final sintering, either, and the transparency and strength of the sintered body were short. In Comparative Example 2, in which the relative density of the microporous preliminarily sintered body was more than the upper limit prescribed in the present disclosure, the sorption inorganic oxide was not able to be fully sorbed in the pores, the transparency of the sintered body was high, but improvement in strength was not seen. In Comparative Example 3, in which the content of aluminum oxide was less than the lower limit prescribed in the present disclosure, high sintered density was not obtained, and the transparency of the sintered body was short. In Comparative Example 4, in which the sorption inorganic oxide was not held in the pores of the microporous preliminarily sintered body, the transparency of the sintered body did not only decrease due to the refractive index difference from zirconium oxide, but the strength also decreased.

As shown in Table 5, the contrast ratios (transparencies) of the finally sintered bodies obtained in Example land Examples 10 to 12 were equivalent to the contrast ratios of the sintered bodies obtained in the corresponding Reference Examples, respectively, but the biaxial flexural strength was improved by 10% or more in any case.

The invention claimed is:

1. A zirconia dental mill blank, comprising a milling target part composed of a composite material, the composite material comprising:

a matrix comprising a preliminarily sintered body of crystalline zirconium oxide powder comprising a stabilizer and an aluminum oxide additive; and fine particles of an inorganic oxide, provided that zirconium oxide, an inorganic oxide functioning as a stabilizer, and aluminum oxide are excluded, wherein, in the composite material, the preliminarily sintered body is a microporous preliminarily sintered body having a relative density of 45 to 65% and having pores opened outward, and the fine particles of the inorganic oxide are held in the pores of the microporous preliminarily sintered body, an average primary particle diameter of the fine particles of an inorganic oxide is 2 nm to 100 nm, and a content ratio of the fine particles of the inorganic oxide held in the pores of the microporous preliminarily sintered body is 0.09 to 10% by mass based on a total mass of the microporous preliminarily sintered body and the fine particles of the inorganic oxide.

2. The zirconia dental mill blank according to claim 1, wherein an average pore diameter of the microporous preliminarily sintered body measured by mercury penetration is in a range of 50 to 200 nm, and the fine particles of the inorganic oxide have the average primary particle diameter smaller than the average pore diameter.

3. A method for manufacturing the zirconia dental mill blank according to claim 1, comprising:

a matrix manufacturing step of molding the crystalline zirconium oxide powder into a predetermined shape, and then preliminarily sintering the molded powder at 600 to 1200° C. to obtain the matrix;

a sorption step of immersing the matrix obtained in the matrix manufacturing step in a sol in which the fine particles of the inorganic oxide are dispersed in a dispersion medium and a concentration of the fine particles is 0.03 to 0.9% by mass based on a mass of the sol, to thereby sorb the fine particles of the inorganic oxide in the pores of the microporous preliminarily sintered body constituting the matrix; and a drying step of removing the dispersion medium from the matrix subjected to the sorption step.

4. A method for manufacturing a dental zirconia ceramic prosthesis composed of a zirconia composite ceramic, wherein the zirconia composite ceramic has, as a basic structure, a structure in which aluminum oxide crystal grains as an additive are dispersed in a polycrystal structure formed by bonding of the same or different types of zirconia crystals in which a stabilizer is solid dissolved, and further comprises an inorganic oxide, provided that zirconium oxide, an inorganic oxide functioning as a stabilizer, and aluminum oxide are excluded, a content ratio of the inorganic oxide contained in the zirconia composite ceramic is 0.09 to 10% by mass based on a mass of the zirconia composite ceramic, and in the basic structure, the inorganic oxide exists in at least one selected from a grain boundary between zirconia crystal grains adjoining each other and a grain boundary between a zirconia crystal grain and an aluminum oxide crystal grain adjoining, the manufacturing method comprising:

a milling step of milling a milling target part of the zirconia dental mill blank according to claim 1 using a CAD/CAM system to obtain a semifinished product having a shape corresponding to a shape of a target dental prosthesis and composed of the composite material; and a final sintering step of sintering the semifinished product at a temperature of more than 1200° C. and 1800° C. or less to change the composite material into the zirconia composite ceramic.

5. The manufacturing method according to claim 4, wherein biaxial flexure strength of the zirconia composite ceramic measured according to JIS T6526:2018 is 800 to 2000 MPa, and a contrast ratio is 0.5 to 0.8, the contrast ratio being an index of transparency, and being defined by the following expression:

$$\text{contrast ratio} = Yb/Yw$$

wherein Y means Y values obtained from a sample having a thickness of 1.0 mm±0.01 mm by spectral reflectance measurement using a spectrophotometer, and Yb and Yw represent the Y values measured with a background color black and a background color white, respectively.

* * * * *